United States Patent [19]

Chang

[11] Patent Number: 4,681,708

[45] Date of Patent: Jul. 21, 1987

[54] PROCESS FOR CONVERTING AN ALKOXYALKADIENE TO AN ALKYL DIALKOXYALKANOATE

[75] Inventor: Biau-Hung Chang, West Chester, Ohio

[73] Assignee: National Distillers and Chemical Corporation, New York, N.Y.

[21] Appl. No.: 914,906

[22] Filed: Oct. 3, 1986

[51] Int. Cl.$^4$ .................. C07C 67/37; C07C 67/38
[52] U.S. Cl. .................. 260/410.9; 560/186
[58] Field of Search .......... 260/410.9 Q; 560/186; 568/689

[56] References Cited

U.S. PATENT DOCUMENTS

| | | | |
|---|---|---|---|
| 3,036,100 | 5/1962 | Pfeiffer et al. | 260/410.9 Q |
| 3,112,330 | 11/1963 | Oughton | 260/410.9 Q |
| 3,140,303 | 7/1964 | De LaMare et al. | 260/410.9 Q |
| 3,156,714 | 11/1964 | Surmatis | 260/410.9 Q |
| 3,330,840 | 7/1967 | Pryde et al. | 260/410.9 Q |
| 3,499,042 | 3/1970 | Smutny | 568/690 |
| 3,670,029 | 6/1972 | Roman et al. | 568/689 |
| 4,138,418 | 2/1979 | Warning et al. | 560/186 |
| 4,311,862 | 1/1982 | Drent | 568/689 |

FOREIGN PATENT DOCUMENTS 688555 3/1953 United Kingdom ............... 560/186

*Primary Examiner*—J. E. Evans
*Attorney, Agent, or Firm*—Kenneth D. Tremain

[57] ABSTRACT

A process for converting an alkoxyalkadiene to an alkyl dialkoxyalkanoate is disclosed. The process involves contacting an alkoxyalkadiene with carbon monoxide and an alkanol in the presence of a catalytically effective amount of a cobalt catalyst.

18 Claims, No Drawings

PROCESS FOR CONVERTING AN ALKOXYALKADIENE TO AN ALKYL DIALKOXYALKANOATE

BACKGROUND OF THE DISCLOSURE

1. Field of the Invention

The present invention is directed to a process for converting an alkoxyalkadiene to an alkyl dialkoxyalkanoate More specifically, the present invention is directed to a process for converting an alkoxyalkadiene to an alkyl dialkoxyalkanoate by contacting the alkoxyalkadiene with carbon monoxide and an alkanol in the presence of a cobalt catalyst.

2. Background of the Prior Art

Alkyl dialkoxyalkanoates can be effectively utilized as intermediates in the synthesis of important compounds which are either not formable by synthetic means or if formable, can be synthesized only at uncommercial, high cost. For example, no satisfactory process has yet been discovered for synthesizing azelaic acid and its esters in a commercially exploitable process. This omission in the art has retarded the development of new commercial routes to the formation of such commercially important products as azelaic acid and esters thereof.

Yamahara et al., Japanese Patent Publication No. 53-37326 discloses a process for the hydrolysis of allylic ethers by reacting the ether with water in the presence of a ruthenium compound to produce an aldehyde. Among the allylic ethers suggested by Yamahara et al. is 1-methoxyoctadiene-2,7. This is an alternative nomenclature for reciting the more generally used name of the compound 8-methoxy-1,6-octadiene, a compound within the generic class of alkoxyalkadienes.

U.S. Pat. No. 3,427,344 describes a process in which an allylic compound, including an allylic ether is reached with carbon monoxide and a cyclic ether in the presence of a noble metal catalyst selected from Group VII or Group VIII to produce an unsaturated carboxylic acid ester.

Neither of these references disclose a process which produces an alkyl dialkoxyalkanoate. This brief description emphasizes the need in the art for a new process to produce the desirable class of compounds, the alkyl dialkoxyalkanoates.

SUMMARY OF THE INVENTION

A new process has now been discovered which provides a one-step reaction for converting an alkoxyalkadiene to form an alkyl dialkoxyalkanoate.

In accordance with the present invention a process is provided for synthesizing an alkyl dialkoxyalkanoate wherein an alkoxyalkadiene is contacted with an alkanol and carbon monoxide in the presence of a catalytically effective amount of a cobalt catalyst.

DETAILED DESCRIPTION

One of the reactants of the process of the present invention is an alkanol. The preferred alkanols of the present invention contain 1 to about 10 carbon atoms. More preferably, the alkanols of the present invention contain 1 to about 6 carbon atoms. More preferably, the alkanols of the present invention contain 1 to 4 carbon atoms. Still more preferably, the alkanols employed in the process of the present invention contain 1 to about 2 carbon atoms. Most preferably, the alkanol of the present invention is methanol.

A second reactant employed in the process of this invention, an alkoxyalkadiene, encompasses an alkoxy substituent usually having between 1 and about 10 carbon atoms substituted on an alkadiene usually containing between 4 and about 12 carbon atoms.

Preferably, the alkoxy substituent is positioned at the n position where n is an integer equal to the number of carbon atoms in the alkadiene chain. It should be appreciated, however, that although the alkadiene chain may be substituted the number of carbon atoms does not include carbon atoms on substituents. It should be appreciated, however, that the alkadiene chain is preferably not substituted. In this preferred embodiment, wherein there are no substituents other than alkoxy, the alkoxyalkadiene has the formula n-alkoxyalkadiene.

More preferably, the alkoxyalkadiene includes an alkoxy containing 1 to about 6 carbon atoms and an alkadiene containing 4 to about 10 carbon atoms.

Still more preferably, the alkoxyalkadiene comprises an alkoxy having 1 to about 4 carbon atoms and an alkadiene having 4 to about 8 carbon atoms.

Most preferably, the alkoxyalkadiene incorporates an alkoxy of 1 or 2 carbon atoms and the alkadiene is octadiene.

The diene reactant of the present invention, the alkoxyalkadiene, is synthesizable from readily available starting materials. For example, 8-alkoxy-1,6-octadiene can be readily formed by telomerization of butadiene with an alkanol. The alkanol used in this telomerization reaction usually contains 1 to about 10 carbon atoms with 1 to about 6 carbon atoms being preferred. More preferably, the alkanol is one containing 1 to about 4 carbon atoms. Still more preferably, the alkanol contains 1 to about 2 carbon atoms with methanol being particularly preferred.

The resultant product of this telomerization reaction is 8-alkoxy-1,6-octadiene. The identity of the alkoxy is dependent upon the alkanol employed in the telomerization reaction. In a particularly preferred embodiment of the present invention corresponding to the embodiment wherein methanol is the alkanol of the telomerization reaction, the diene reactant of the process of this invention is 8-methoxy-1,6-octadiene.

A third reactant in the process of the present invention is the gas, carbon monoxide. This gas not only serves as an essential reactant but, in addition, acts to at least partially provide the desired pressure of reaction. Therefore, the carbon monoxide is usually introduced at superatmospheric pressure.

The reaction between the alkoxyalkadiene, carbon monoxide and the alkanol occurs in the presence of a cobalt catalyst. The cobalt catalyst of the present invention may be metallic cobalt, a cobalt salt or a cobalt coordination compound.

In the preferred embodiment wherein a cobalt salt is employed, a cobalt halide and a cobalt alkanoate are preferred. Of the cobalt halides, cobalt chloride finds particular application.

The cobalt coordination compounds of the present invention are usually cobalt carbonyl complexes. In the case where a cobalt carbonyl complex is employed it is preferable, although not essential, to add a phosphine, a phosphite or a nitrogen-containing compound. Among the nitrogen-containing compounds, aliphatic amines and aromatic nitrogen-containing heterocyclic compounds are particularly preferred. Of the aliphatic amines, triethylamine is particularly preferred. Of the nitrogen-containing heterocyclic compounds, pyridine is particularly applicable.

A particularly preferred cobalt catalyst within the contemplation of the present invention is the cobalt carbonyl complex comprising $Co_2(CO)_8$ and pyridine.

The process of the present invention preferably occurs at a pressure in the range of between about 1,000 and 5,000 psig. As stated above, this pressure is conveniently provided in whole or in part by an essential component in the process of this invention, carbon monoxide. In a preferred embodiment it is desirable to include hydrogen gas in the reaction. Although the partial pressure of the hydrogen gas is relatively minor, compared to that of carbon monoxide, its presence improves the effectiveness of the process of this invention. The preferred temperature range of the process of the present invention is between about 90° C. and about 200° C.

More preferably, the process of the present invention is conducted at a pressure in the range of between about 1,000 psig to about 2,000 psig and at a temperature in the range of between about 120° C. and about 200° C. under anhydrous conditions.

The following example is given to illustrate the scope of the present invention. Because this example is given for illustrative purposes only, the present invention should not be limited thereto.

EXAMPLE

The following liquids were introduced into an 8 ounce bottle; 65.0 g. (0.464 mol) 8-methoxy-1,6-octadiene; 59.43 g. (0.139 mol) methanol; and 11.02 g. (0.139 mol) pyridine. This mixture was charged into a 300 ml. stirred reactor which had been earlier purged with nitrogen. The mixture was added under a nitrogen blanket. In addition, 3.17 g. (9.27 mmols) of $Co_2(CO)_8$, held in a vial, was separately added into the stirred reactor under a nitrogen blanket.

The reactor was sealed and purged three times with carbon monoxide. The reactor was then pressurized to 40 psig with hydrogen gas followed by an increase to 1,500 psig by the addition of carbon monoxide gas. The reactor was stirred for 2 to 3 minutes and the temperature and pressure of the reactor were then increased to 180° C. and 2,000 psig, respectively. The reaction was conducted for 5 hours measured from the time the reactor reached 2,000 psig and 180° C. It is noted that the reaction was maintained at 2,000 psig by regulating the pressure with carbon monoxide.

The product was analyzed by gas chromotography and found to contain 17.7% of the desired product, methyl 9,9-dimethoxynonanoate.

The above embodiments and example are given to illustrate the scope and spirit of the present invention. These embodiments and example will make apparent, to those skilled in the art, other embodiments and examples. These other embodiments and examples are within the contemplation of the present invention. Therefore, the present invention should be limited only by the appended claims.

What is claimed is:

1. A process for forming an alkyl dialkoxyalkanoate comprising contacting an alkoxyalkadiene with an alkanol and carbon monoxide in the presence of a catalytically effective amount of a cobalt catalyst.

2. A process in accordance with claim 1 wherein said alkoxyalkadiene is characterized by a substituent alkoxy having 1 to about 10 carbon atoms substituted on an alkadiene having 4 to about 12 carbon atoms.

3. A process in accordance with claim 2 wherein said alkoxyalkadiene is n-alkoxyalkadiene wherein n is an integer equal to the number of carbon atoms of said alkadiene.

4. A process in accordance with claim 3 wherein said alkoxy contains 1 to about 6 carbon atoms and said alkadiene contains 4 to about 10 carbon atoms.

5. A process in accordance with claim 4 wherein said alkoxy contains 1 or 2 carbon atoms and said alkadiene is octadiene.

6. A process in accordance with claim 2 wherein said alkanol contains 1 to about 10 carbon atoms.

7. A process in accordance with claim 1 wherein said cobalt catalyst is selected from the group consisting of metallic cobalt, a cobalt salt and a cobalt coordination compound.

8. A process in accordance with claim 7 wherein said cobalt catalyst is a cobalt halide.

9. A process in accordance with claim 8 wherein said cobalt halide is cobalt chloride.

10. A process in accordance with claim 7 wherein said cobalt catalyst is a cobalt carbonyl complex.

11. A process in accordance with claim 10 wherein said cobalt carbonyl complex includes a ligand selected from the group consisting of a phosphine compound, a phosphite compound and a nitrogen-containing compound.

12. A process in accordance with claim 11 wherein said cobalt catalyst comprises a complex formed from $Co_2(CO)_8$ and pyridine.

13. A process in accordance with claim 1 wherein said process occurs at a temperature in the range of between about 90° C. and about 200° C. and at a pressure in the range of between about 1,000 psig and about 5,000 psig.

14. A process in accordance with claim 13 wherein said process occurs under anhydrous conditions at a temperature in the range of between about 120° C. and about 200° C. and at a pressure in the range of between about 1,000 psig and about 2,000 psig.

15. A process in accordance with claim 1 wherein said process occurs in the presence of hydrogen gas.

16. A process for forming an alkyl dialkoxynonanoate comprising contacting an alkoxyoctadiene with carbon monoxide and an alkanol at a temperature in the range of between about 90° C. and about 200° C. and at a pressure in the range of between about 1,000 psig and about 5,000 psig in the presence of catalytically effective amount of a cobalt coordination complex.

17. A process in accordance with claim 16 wherein said alkoxyoctadiene is 8-alkoxy-1,6-octadiene, said alkanol is methanol and said cobalt coordination complex is formed in-situ from $Co_2(CO)_8$ and pyridine.

18. A process in accordance with claim 17 wherein said process occurs under anhydrous conditions in the presence of hydrogen gas, at a temperature in the range of between about 120° C. and about 200° C. and at a pressure in the range of between about 1,000 psig and about 2,000 psig.

* * * * *